United States Patent
Leroi et al.

(10) Patent No.: US 11,072,529 B2
(45) Date of Patent: Jul. 27, 2021

(54) CATALYTIC CONVERSION OF DSO IN PRESENCE OF WATER

(71) Applicant: TOTAL SA, Courbevoie (FR)

(72) Inventors: Catherine Leroi, Pau (FR); Claire Weiss, Vaucresson (FR); Renaud Cadours, Franchville (FR); Claudia Cammarano, Montpellier (FR); Vasile Hulea, Montpellier (FR)

(73) Assignee: TOTAL SA, Courbevoie (FR)

( * ) Notice: Subject to any disclaimer, the term of this patent is extended or adjusted under 35 U.S.C. 154(b) by 0 days.

(21) Appl. No.: 16/344,987

(22) PCT Filed: Oct. 27, 2016

(86) PCT No.: PCT/IB2016/001706
§ 371 (c)(1),
(2) Date: Apr. 25, 2019

(87) PCT Pub. No.: WO2018/078410
PCT Pub. Date: May 3, 2018

(65) Prior Publication Data
US 2019/0270642 A1    Sep. 5, 2019

(51) Int. Cl.
| | |
|---|---|
| C01B 17/16 | (2006.01) |
| C07C 1/32 | (2006.01) |
| B01J 21/04 | (2006.01) |
| B01J 8/02 | (2006.01) |
| B01J 4/00 | (2006.01) |
| C10L 3/10 | (2006.01) |

(52) U.S. Cl.
CPC ............. *C01B 17/165* (2013.01); *B01J 4/001* (2013.01); *B01J 8/02* (2013.01); *B01J 21/04* (2013.01); *C07C 1/322* (2013.01); *C10L 3/103* (2013.01); *C07C 2521/04* (2013.01); *C10L 2290/12* (2013.01); *C10L 2290/141* (2013.01)

(58) Field of Classification Search
CPC .... C07C 1/322; B01J 8/02; B01J 21/04; B01J 4/001; C10L 2290/141; C10L 3/103; C10L 2290/12; C01B 17/165
See application file for complete search history.

(56) References Cited

U.S. PATENT DOCUMENTS

| | | |
|---|---|---|
| 4,265,735 A | 5/1981 | Audeh et al. |
| 5,157,201 A | 10/1992 | Norris |
| 2006/0057056 A1* | 3/2006 | Chretien ............... C10L 3/12 423/573.1 |
| 2016/0144335 A1 | 5/2016 | Catchpole |

OTHER PUBLICATIONS

PCT International Search Report for PCT/M2016/001706 dated Jul. 14, 2017, 4 pages.
PCT Written Opinion of the ISA for PCT/IB2016/001706 dated Jul. 14, 2017, 4 pages.
A V. Mashkina: "Dimthyl disulfide catalytic conversion into methanethiol in the presence of water", Kinetics and Catalysis, vol. 41, No. 2, 2000, pp. 216-221, XP055379787, Russian Federation ISSN: 0023-1584, DOI : 10.1007/BF02771423.
A. V. Mashkina et al: "Activity of catalysts in the synthesis of dimethyl sulfide from dimethyl disulfide", Kinetics and Catalysis, vol. 50, No, 3, 2009, pp. 414-419, XP055379721, Russian, Federation ISSN: 0023-1584, DOI : 10.1134/S002315809030124.
Ding L et al; "Decomposition of dimethyldisulfide on various W—Ni catalysts", Catalysis Commonications, Elsevier, Amsterdam, NL, vol. 7, No. 12, Dec. 2006 (Dec. 2006), pp. 1035-4041, XP024973124, ISSN: 1566-7361, DOI: 10.1016/J.CATCOM.2006. 05.006 [retrieved on Dec. 1, 2006].
A. V. Mashkina: "Catalytic conversions of dialkyl disulfides", Kinetics and Catalysis, vol. 49, No. 6, Nov. 2008 (Nov. 2008), pp. 802-811, XP055379726, Russian Federation ISSN: 0023-1584, DOI: 10.1134/S0023158408060050.
Alacaraz et al. "Solid Base catalysts for mercaptan oxidation", Catal. Today 43 (1998) 89-99.
Mashkina et al., "Catalytic Decomposition of Dimethyl Disulfide", React. Kinet. Cat. Lett. 53 (1994), 363-368.
Mashkina et al., "Conversion of Dimethyl Disulfide in the Presence of Zeolites" Kin. and Catal. 49-2 (2008) 253-260).
J. A. R. Coope, W. A. Bryce, "The Thermal Decomposition of Dimethyl Disulphide", Can. J. Chem.,32-8 (1954) 768-779.

* cited by examiner

*Primary Examiner* — Timothy C Vanoy
(74) *Attorney, Agent, or Firm* — Patterson Thuente Pedersen, P.A.

(57) ABSTRACT

The present invention relates to a method for the catalytic conversion in vapor phase of disulfide oil into methane and hydrogen sulfide, comprising the step of contacting disulfide oil, eventually in the presence of water, with a supported transition metal catalyst.

17 Claims, 8 Drawing Sheets

CATALYTIC CONVERSION OF DSO IN PRESENCE OF WATER

RELATED APPLICATIONS

The present application is a National Phase entry of PCT Application No. PCT/IB2016/001706, filed Oct. 27, 2016, said application being hereby incorporated by reference herein in its entirety.

FIELD OF THE INVENTION

The present invention relates to the catalytic conversion in vapor phase of disulfide oil (DSO), a by-product obtained in oil refineries and natural gas processing plants.

BACKGROUND

Natural gas comprises from 70 to 90% of methane ($CH_4$), the remaining part being impurities such as carbon dioxide ($CO_2$), water ($H_2O$), hydrocarbons and sulfur compounds, mainly hydrogen sulfide ($H_2S$) and mercaptans.

To meet the environmental and industrial process requirements, natural gas must be further purified to remove these impurities. Typically the purification process may comprise a step of dehydration and removal of the acid compounds, $CO_2$ and $H_2S$, and mercaptans. After this first step, natural gas still contains up to 2 wt % of $CO_2$ and from 20 to 50 ppm of total sulfur compounds. The purification process may alternatively comprise a step of amine treatment and dehydration to remove the acid compounds. In both cases, the remaining amounts of mercaptans are too high to meet the specifications of marketable natural gas since, for example, the amount of mercaptans must not be higher than 5 ppm.

For the last decades, different technologies have been developed to further remove mercaptans and reach the above requirements. Said technologies are either based on the adsorption through a fixed bed or on chemical reactions such as oxidation, alkaline treatment, reaction with olefin and hydrodesulfurization.

According to the oxidation reaction technology (Alacaraz et al. Catal. Today 43 (1998) 89-99), mercaptans are contacted with an oxidizer, which leads to the production of an unwanted by-product named disulfide oil (DSO), which is composed of a mixture of dialkyldisulfides. Different kinds of oxidizers may be used, such as sodium plumbite, sulfur, air, hypochlorite, copper chloride, and transition metal complex. DSO is obtained in a huge amount. It is thus important to convert DSO into recoverable product such as $H_2S$ and hydrocarbons, in particular $CH_4$.

A practical process to treat DSO is the oxidation during the elimination of $H_2S$ inside a Claus Unit. A complete conversion of DSO can only be reached with an excess of oxygen, so the amount of DSO diverted and treated in a Claus Unit is rather low. This process is thus no longer used today. Another process to treat DSO is to burn them in excess of oxygen to produce $SO_2$, outside a Claus Unit. After a separation from flue gas with a solvent, $SO_2$ may then be introduced in an existing Claus Unit. However, the reagents and operating conditions during DSO combustion are corrosive and necessitate specific equipment materials increasing the investment and maintenance cost of the device.

DSO can be catalytically converted into recoverable products by being contacted with a catalyst having surface acidity, such as NaX, NaY, HNaY, HZSM5, at a temperature from 190° C. to 350° C. under a mixture containing $H_2$ (U.S. Pat. No. 4,265,735, Mashkina et al., React. Kinet. Cat. Lett. 53 (1994), 363-368 and Mashkina et al., Kin. and Catal. 49-2 (2008) 253-260). Methyl mercaptan, DMS, $H_2S$ and traces of $CH_4$ are obtained. The amount of each product depends on the catalyst and the reaction conditions. For example, in the presence of a water steam, the amount of methyl mercaptan increases, while the amount of dimethylsulfide decreases. However, some of these compounds are not recoverable compounds. Moreover, the catalyst is rapidly deactivated due to the formation of polymer ($CH_2S$), sulfur or coke (J. A. R. Coope, W. A. Bryce, Can. J. Chem., 32-8 (1954) 768-779). A study shows that the addition of cobalt to the catalyst may improve the stability of said catalyst (Mashkina et al., Kin. and Catal. 49-2 (2008) 253-260).

The catalytic conversion of DSO is promising, however, there is still a need to provide an improved method for the catalytic conversion of DSO into recoverable products, such as $CH_4$ and $H_2S$, using a catalyst having a high stability, without using $H_2$ that is expensive and dangerous.

The present invention meets all these needs by providing a method to convert, by catalytic conversion, DSO into $CH_4$ and into $H_2S$. Moreover, the reaction conditions improve the lifetime of the catalyst and do not use $H_2$ as a reagent.

SUMMARY OF THE INVENTION

One object of the invention is a method for the catalytic conversion in vapor phase of disulfide oil into methane and hydrogen sulfide, comprising the step of contacting disulfide oil with a supported transition metal catalyst.

In one embodiment, the step of contacting disulfide oil with the supported transition metal catalyst is performed in the presence of water.

Additionally or alternatively, the supported transition metal catalyst comprises a support chosen from alumina ($Al_2O_3$), silica, titania ($TiO_2$) or a mixture thereof, preferably the support is alumina.

Additionally or alternatively, the alumina is chosen from alpha-alumina, gamma-alumina, delta-alumina, theta-alumina, preferably the alumina is gamma-alumina.

Additionally or alternatively, the transition metal is chosen from manganese, iron, cobalt, nickel, copper, zinc, molybdenum, ruthenium, rhodium or a mixture thereof, preferably the transition metal is cobalt.

Additionally or alternatively, the content of transition metal in the supported transition metal catalyst relative to the support is 0.1 wt % to 10 wt %, in particular 1 wt % to 5 wt %, more particularly 2.2 wt % to 2.7 wt %.

Additionally or alternatively, the molar ratio of water in the vapor phase comprising disulfide oil to disulfide oil is 0.1 to 10, in particular 1 to 7, more particularly 1.4 to 4.

Additionally or alternatively, the step of contacting disulfide oil is performed at a temperature from 350° C. to 700° C., in particular from 525° C. to 575° C., more particularly from 540° C. to 560° C.

Additionally or alternatively, the method further comprising a step of oxidative regeneration of a spent supported transition metal catalyst.

Additionally or alternatively, the oxidative regeneration step is performed in the presence of air.

Another object of the invention is a catalytic conversion unit for carrying out the method described above, comprising a catalytic reactor comprising a vapor feed line to feed the catalytic reactor with a vapor phase of disulfide oil, a gas recover line to recover a gaseous stream comprising methane and H2S, and at least one catalytic bed wherein a supported transition metal catalyst is placed.

Additionally or alternatively, the catalytic conversion unit further comprises a vapor generator unit for generating the vapor phase of disulfide oil and fluidly connected to the vapor feed line of the catalytic reactor, and a liquid feed line to feed the vapor generator unit with liquid disulfide oil.

Additionally or alternatively, the catalytic conversion unit further comprises a water reactor for providing liquid water or water steam to the catalytic conversion unit through a water line.

Additionally or alternatively, the water line is fluidly connected to one or more of the liquid feed line, the vapor generator unit, the vapor feed line and the catalytic reactor.

Additionally or alternatively, the water reactor is fed with the vapor phase of disulfide oil by the vapor feed line and is fluidly connected to the catalytic reactor through the water line.

Additionally or alternatively, the catalytic conversion unit further comprises a separation unit fed by the gas recover line of the catalytic reactor for separating methane from hydrogen sulfide of the gaseous stream, a methane line to recover methane, and a hydrogen sulfide line to recover hydrogen sulfide.

Additionally or alternatively, the catalytic conversion unit further comprises a sulfur recovery unit fed by the hydrogen sulfide line and having a sulfur exit line for recovering elemental sulfur and a gas exit line for recovering a tail gas stream.

DETAILED DESCRIPTION OF THE INVENTION

Method

One object of the invention is a method for the catalytic conversion in vapor phase of disulfide oil into methane and hydrogen sulfide, comprising the step of contacting disulfide oil with a supported transition metal catalyst.

According to the present invention, gaseous methane ($CH_4$) and $H_2S$ are the main products of the catalytic conversion of disulfide oil (DSO) in vapor phase. Advantageously, $CH_4$ and $H_2S$ are recoverable products.

Disulfide oil is a mixture of dialkyldisulfides such as dimethyldisulfide (DMDS), diethyldisulfide (DEDS), and methyldisulfide (MEDS). It is an extremely flammable substance with a relatively high vapor pressure and low water solubility. At room temperature, DSO exists as a yellow liquid.

In one embodiment, DSO consists essentially of DMDS, DEDS or a mixture thereof.

In one embodiment, DSO comprises from 20 mol % to 100 mol % of DMDS and from 0 mol % to 80 mol % of DEDS, in particular from 60 mol % to 100 mol % of DMDS and from 0 mol % to 40 mol % of DEDS.

Since DMDS is the main compound of DSO, DMDS is considered as a model molecule for DSO in the field of the present invention. Therefore, in the present application, all the features and embodiments related to DSO equally apply to DMDS.

According to the invention, the step of contacting DSO, with the supported transition metal catalyst is performed in vapor phase, i.e. with gaseous reactant in a catalytic reactor while the catalyst is solid, typically in powder or granulates form.

According to the present invention, the vapor phase comprises DSO in gaseous form.

These particular reactional conditions lead advantageously to the complete conversion of DSO and the formation of $CH_4$ with reduced or without formation of by-products such as methanethiol and dimethylsulfide (DMS).

Typically, the vapor phase comprising DSO may be obtained in a vapor generator unit by vaporizing liquid DSO or by enriching a neutral gaseous stream in DSO.
The liquid DSO may be vaporized at operating conditions and by technologies known by the skilled person. Such technologies are the ones using a heat exchanger wherein the heat is provided by a hot fluid, a vaporizer wherein heat is provided by a gaseous stream, a boiler or a reboiler directly providing the heat, or a steam generator producing heat from the combustion of residual gas or liquid.

The neutral gas stream may be enriched in DSO by passing said neutral gaseous stream through a reactor comprising liquid DSO. Typically, the neutral gaseous stream may be chosen from a nitrogen gaseous stream, a helium gaseous stream, an argon gaseous stream, a methane gaseous stream or a mixture thereof.

Typically, liquid DSO may be obtained by the oxidation of mercaptans in a conventional mercaptans treatment unit.

In one embodiment of the invention, the step of contacting DSO with the supported transition metal catalyst is performed in presence of water.

Advantageously, the presence of water not only leads to the formation of $CH_4$ without formation of methanethiol or DMS but also leads to the increase of $H_2S$. Indeed $H_2S$ may be obtained by the hydrolysis of products resulting from the conversion of DSO and comprising sulfur by the supported transition metal catalyst. Therefore, the presence of water increases the amount of recoverable products formed by the catalytic conversion of DSO.

Another advantage of the presence water is the increase of the stability of the supported transition metal catalyst. Without being bound by any theory, the inventors found that the presence of water reduces the amount of coke deposited on the surface of the supported transition metal catalyst thereby avoiding its deactivation and increasing its stability. Indeed, it is well known that coke deposition is a major cause of catalyst deactivation. Moreover, since the stability of the supported transition metal catalyst is increased, its lifetime is also increased.

According to one embodiment, a water steam is directly introduced in the catalytic reactor wherein the step of contacting DSO, with the supported transition metal catalyst is performed. As a result, water steam contacts directly the supported transition metal catalyst.

According to one embodiment, water steam is present in the vapor phase comprising DSO and is thus introduced in the catalytic reactor together with said vapor phase.

A vapor phase comprising DSO and water steam may be obtained by the several different processes. Typically, the vapor phase comprising DSO and water steam may result from the mixing of a water steam with a vapor phase comprising DSO, for example by well-known gas mixer such as static mixer. The vapor phase may also be obtained by enriching a water steam in DSO, for example by passing said water steam through a reactor comprising liquid DSO, or by enriching a vapor phase comprising DSO in water, for example by passing said vapor phase comprising DSO through a water reactor comprising liquid water. The vapor phase comprising DSO and water steam can also be obtained by vaporizing a liquid mixture of DSO and water. In this latter case, the liquid mixture of DSO and water may typically be vaporized at operating conditions and by technologies known by the skilled person. Such technologies are the ones using a heat exchanger wherein the heat is provided by a hot fluid such, a vaporizer wherein heat is provided by a water steam or a gaseous stream, a boiler or a reboiler directly providing the heat, or a steam generator producing heat from the combustion of residual gas or liquid.

Typically, the water steam or liquid water may be provided from a water reactor through a water line.

In one embodiment, the molar ratio of water in the vapor phase comprising disulfide oil to disulfide oil is 0.1 to 10, in particular 1 to 7, more particularly 1.4 to 4.

According to one embodiment, the step of contacting DSO is performed at a temperature from 350° C. to 700° C., in particular from 525° C. to 575° C., more particularly from 540° C. to 560° C.

In the above range of temperature, the catalytic conversion of DSO is advantageously complete. Moreover, if the temperature is lower, non-recoverable product such as methanethiol or DMS might be obtained and, if the temperature is higher, then the process is expensive since it needs special alloys, such as refractory alloys.

As mentioned above, the catalytic conversion of DSO is performed using the supported transition metal catalyst.

As used herein, the term "supported transition metal catalyst" refers to a catalyst comprising a transition metal as an active catalytic material and a support, said transition metal being dispersed upon said support.

A transition metal is an element belonging to the Group IIIb, IVb, Vb, VIb, of Lanthanides or Actinide of the Periodic Table of the Elements. It is believed that substantially all of the transition metal exists within the supported transition metal catalyst in the oxidized state. Therefore, the transition metal may be introduced in the catalytic reactor in its oxidized form.

Typically, the support of the supported transition metal catalyst may be chosen from alumina ($Al_2O_3$), silica, titania ($TiO_2$), or a mixture thereof, preferably the support is alumina.

Alumina is preferred as a support for the catalyst since it combines favorable characteristics such as a refractory property and a mesoporosity. Indeed, due to its refractory property, $Al_2O_3$ has a high mechanical resistance to prevent sintering of the catalyst during the catalytic conversion of DSO. Moreover, without being bound by any theory, the inventors found that the mesoporosity of the alumina limits the deactivation of the supported transition metal catalyst by avoiding the clogging of the pores of said catalyst by the coke, thereby increasing its stability and its lifetime.

In one embodiment, the alumina is chosen from alpha-alumina, gamma-alumina, delta-alumina, theta-alumina, preferably the alumina is gamma-alumina.

It is known that DSO can be catalytically converted by being contacted with a catalyst having surface acidity. Advantageously, gamma-alumina is the alumina having the highest surface acidity.

Typically, the transition metal of the supported transition metal catalyst may be chosen from manganese, iron, cobalt, nickel, copper, zinc, molybdenum, ruthenium, rhodium or a mixture thereof, preferably the transition metal is cobalt.

The addition of cobalt to the support advantageously increases the amount of $CH_4$ formed by the complete catalytic conversion of DSO.

If the step of contacting DSO with the supported transition metal catalyst is performed in presence of water, then the addition of cobalt to alumina advantageously increases the amount of $CH_4$ and $H_2S$ and substantially decreases the amounts of methanethiol and DMS formed by the complete catalytic conversion of DSO.

The content of transition metal in the supported transition metal catalyst relative to the support may be 0.1 wt % to 10 wt %, in particular 1 wt % to 5 wt %, more particularly 2.2 wt % to 2.7 wt %.

These ranges of transition metal content appear to be the best balance between the activity of the catalyst and its cost. Indeed, if the content of transition metal in the catalyst is above these ranges, the alumina support might be coated by more than one layer of transition metal, thereby increasing the price of the catalyst without increasing its activity. On the contrary, if the content of transition metal in the catalyst is lower, the transition metal coating on the alumina support might not be fully achieved, thereby decreasing its activity.

The supported transition metal catalyst may be synthesized by any synthesis techniques known by the skilled person. Such techniques are, for example, co-precipitation, co-gelation, ion exchange, impregnation, or deposition from a vapor phase or from an atomic source. The preferred method is the impregnation of the alumina support with a solution or suspension of the transition metal. According to this preferred method, an inorganic salt of the transition metal such as, for example, acetate, carbonate, chloride, nitrate or sulfate, is dissolved in water to obtain a salted solution. The salted solution has a transition metal amount corresponding to the desired final weight percentage of transition metal on the alumina support. The solution is dropped onto the support, then recovered to be dried, and finally calcinated at high temperature so as to obtain the supported transition metal catalyst.

In one embodiment, the specific surface of the supported transition metal catalyst is at least 150 m$^2$/g, in particular the specific surface is from 200 m$^2$/g to 250 m$^2$/g, more particularly is from 220 m$^2$/g to 230 m$^2$/g.

In one embodiment, the particle size of the supported transition metal catalyst is at least 100 µm, in particular the particle size is from 125 µm to 300 µm, more particularly is from 150 µm to 250 µm.

Like most of the catalysts, the supported transition metal catalyst of the present invention may deactivate with time. Advantageously, the activity of a spent supported transition metal catalyst may be restored by a step of oxidative regeneration. The activity may even be improved by the step of oxidative regeneration.

Typically, the oxidative regeneration of the spent supported transition metal catalyst may be performed in-situ or ex-situ.

During the oxidative regeneration, the spent transition metal supported on alumina is heated to a temperature from 200° C. to 600° C., in the presence of oxygen so as to burn the coke deposited on the surface of the spent supported transition metal catalyst.

The temperature and the partial pressure of oxygen must be controlled to burn all the coke without altering the properties of the supported transition metal catalyst, in particular its porosity.

In an embodiment, the temperature is increased, by 50° C. increments, from 200° C. to 600° C.

Advantageously, this temperature protocol facilitates the control of the exothermicity of the coke combustion, thereby avoiding the decrease of the porosity of the supported transition metal catalyst.

In order to perform the oxidative regeneration, the spent transition metal supported on alumina is subjected to an oxidative gaseous stream. The oxidative gaseous stream may be air, pure or mixed with additional oxygen or an inert gas, such as nitrogen or helium, in order to increase or decrease the oxygen partial pressure.

In a particular embodiment, the oxidative regeneration step is performed in the presence of air.

Advantageously, the use of air to perform the oxidative regeneration of the catalyst is cost saving and facilitates the control of the exothermicity of the coke combustion, thereby avoiding the decrease of the porosity of the supported transition metal catalyst.

Catalytic Conversion Unit

Another object of the present invention is a catalytic conversion unit for carrying out the above disclosed method of the invention. Said catalytic conversion unit is described in more details by referring to FIGS. 1, 2 and 3 and comprises a catalytic reactor 1 comprising a vapor feed line 2 to feed the catalytic reactor 1 with a vapor phase of DSO, a gas recover line 3 to recover a gaseous stream comprising CH$_4$ and H2S, and at least one catalytic bed wherein a supported transition metal catalyst is placed.

Figure 1:
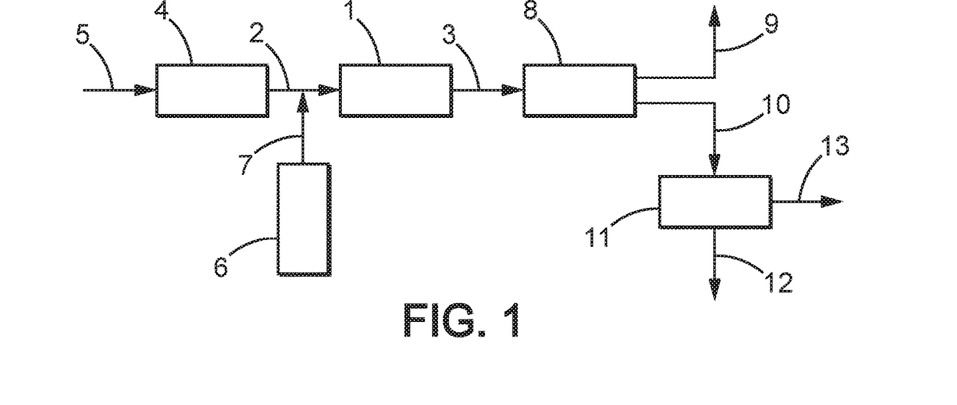
FIGS. 1, 2 and 3 are schematic representations of three embodiments of the process and catalytic conversion unit of the invention.
Figure 2:
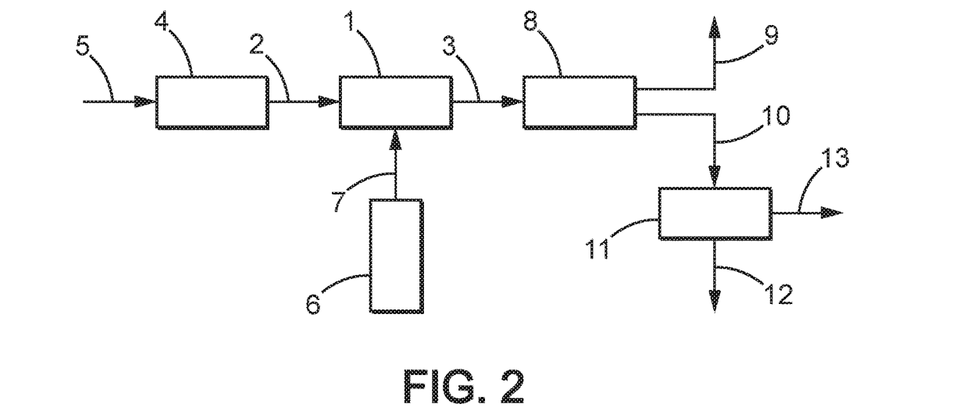
Figure 3:
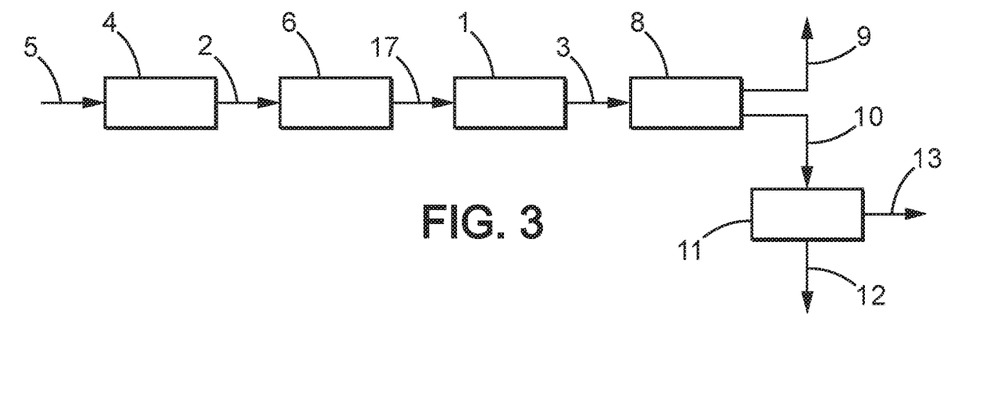

As mentioned above, the step of contacting DSO with the supported transition metal catalyst is performed in the catalytic reactor 1.

The catalytic reactor 1 may be a continuous reactor or a batch reactor. Fixed-bed reactor, reverse flow tubular reactors or fluidized bed reactors are suitable continuous reactors. A fixed-bed reactor is preferred.

Typically a catalytic continuous reactor may comprise the vapor feed line 2, the gas recover line 3 and at least one catalytic bed. The vapor phase of DSO is introduced into the continuous reactor by the vapor feed line 2, flows through the continuous reactor to the catalytic bed, wherein the supported transition metal catalyst is placed. The vapor phase of DSO is thereby contacted with the supported transition metal catalyst and converted into a gaseous stream comprising CH$_4$. The gaseous stream flow from the catalytic bed, through the catalytic reactor 1, to the gas recover line 3 to be recovered.

Typically a catalytic batch reactor may comprise the vapor feed line 2, the gas recover line 3, at least one a catalytic bed and a stirrer. The vapor feed line 2 and the gas recover line 3 may be the same. After the supported transition metal catalyst is placed in the catalytic bed, the catalytic batch reactor 1 is hermetically closed. The vapor feed line 2 is opened so as to introduce the vapor phase of DSO into the batch reactor until the desired amount of vapor phase is introduced. The amount of vapor phase introduced may be controlled by a gas flow meter or by monitoring the internal pressure inside the batch reactor. Indeed the internal pressure depends on the amount of gaseous products inside the catalytic batch reactor. While being introduced, the vapor phase is contacted with the supported transition metal catalyst to be converted into gaseous stream comprising CH$_4$ and H2S. The stirrer mixes the gaseous atmosphere so as to improve the rate of conversion. The conversion reaction may be followed by monitoring the pressure inside the batch reactor. At the end of the conversion reaction, the gas recover line 3 is open so as to recover the gaseous stream.

A continuous catalytic reactor is preferred because the reaction parameters (residence time, temperature and pressure) are better controlled than in a batch reactor, consequently the catalytic reactions is better controlled and monitored. A continuous catalytic reactor also produces less waste and requires much lower storage of both reactants and products resulting in a more efficient operation. Therefore, the capital costs per ton of product produced are lower.

According to one embodiment, the catalytic conversion unit further comprises a vapor generator unit 4 for generating the vapor phase of DSO and fluidly connected to the vapor feed line 2 of the catalytic reactor 1, and a liquid feed line 5 to feed the vapor generator unit 4 with liquid DSO.

The vapor generator unit 4 may be an heat exchanger wherein the heat is provided by a hot fluid, vaporizers wherein heat is provided by a gaseous stream, boiler or reboiler directly providing the heat, or steam generator producing heat from the combustion of residual gas or liquid so that the vapor phase comprising DSO may be obtained by vaporizing liquid DSO.

The vapor generator unit 4 may also be a reactor comprising liquid DSO and fluidly connected to a neutral gaseous line so that a neutral gaseous stream may be enriched in DSO by passing through the reactor comprising liquid DSO thereby obtaining the vapor phase comprising DSO.

According to a specific embodiment, the step of contacting DSO with the supported transition metal catalyst may be performed in presence of water. The catalytic conversion unit of the present invention may thus further comprise a water reactor 6 for providing liquid water or water steam to the catalytic conversion unit through a water line 7.

According to a specific embodiment, the water line 7 is fluidly connected to one or more of the liquid feed line 5, the vapor generator unit 4, the vapor feed line 2 and the catalytic reactor 1.

According to the specific embodiment illustrated in FIG. 1, the water line 7 is fluidly connected to the vapor feed line 2 and water steam from the water reactor 6 is mixed with the vapor phase comprising DSO of the vapor feed line 2 so as to obtain the vapor phase comprising DSO and water steam. To improve the mixing between the water steam and the vapor phase comprising DSO, the vapor feed line 2 may further comprise a gas mixer such as static mixer.

According to another specific embodiment, the water line 7 is fluidly connected to the liquid feed line 5, and liquid water from the water reactor 6 is mixed with liquid DSO before being introduced in the vapor generator unit 4 to obtain a liquid mixture of DSO and water. This liquid mixture of DSO and water is vaporized by the vapor generator unit 4 to obtain the vapor phase comprising DSO and water steam. The catalytic reactor 1 is then fed by the vapor feed line 2 with the vapor phase comprising DSO and water steam. According to this specific embodiment, the vapor generator unit 4 may be a heat exchanger wherein the heat is provided by a hot fluid, a vaporizer wherein heat is provided by a gaseous stream, a boiler or reboiler directly providing the heat, or a steam generator producing heat from the combustion of residual gas or liquid.

According to another specific embodiment, the water line 7 is fluidly connected to the vapor generator unit 4, and the vapor generator unit 4 is a reactor comprising liquid DSO and a water steam from the water reactor 6 is enriched in DSO by passing through the reactor comprising liquid DSO to obtain the vapor phase comprising DSO and water steam. According to this specific embodiment, the catalytic reactor 1 is fed by the vapor feed line 2 with the vapor phase comprising DSO and water steam.

According to the specific embodiment illustrated in FIG. 2, the water line 7 is fluidly connected to the catalytic reactor 1, and the catalytic reactor 1 is fed with water steam from the water reactor 6 so that said water steam contacts directly the supported transition metal catalyst placed on the at least one catalytic bed.

According to this above specific embodiment, the number of water lines 7 fluidly connected to the catalytic reactor 1 depends on the number m of catalytic beds comprised in the catalytic reactor 1. Indeed at least one water line 7 is fluidly connected to said catalytic reactor 1 in the vicinity of each of the m catalytic beds so that water steam contacts directly the transition metal support on alumina catalyst placed on each of the m catalytic beds.

According to a specific embodiment, the water reactor 6 is fed with the vapor phase comprising DSO by vapor line 2 and is fluidly connected to the catalytic reactor 1 through the water line 7.

As illustrated in FIG. 3, the vapor phase comprising DSO thus passes through the water reactor 6 comprising liquid water, thereby being enriched in water, and then is introduced, by a water enriched DSO line 17, in the catalytic reactor 1.

Accordingly the catalytic conversion unit may further comprise a separation unit 8 fed by the gas recover line 3 of the catalytic reactor 1 for separating $CH_4$ from $H_2S$ of the gaseous stream, a methane line 9 to recover methane, and a hydrogen sulfide line 10 to recover hydrogen sulfide.

Advantageously, the separation unit 8 may be a gas treatment unit using solvent, for example amine solvent.

Advantageously, by separating $CH_4$ from $H_2S$ it is possible to recover said gases. For example $CH_4$ may be marketed or injected into a stream of natural gas to be marketed, while $H_2S$ may further be treated in a sulfur recovery unit 11, such as a Claus unit, to produce elemental sulfur used for manufacturing sulfuric acid, medicine, cosmetics, fertilizers, rubber products, fertilizer and pesticide.

The catalytic conversion unit may thus further comprise a sulfur recovery unit 11 feed by the hydrogen sulfide line 10 and having a sulfur exit line 12 for recovering elemental sulfur and a gas exit line 13 for recovering a tail gas stream.

In one embodiment, the gas recover line 3 is recycled back to existing acid gas processing units such as an acid gas removal unit, a sulfur recovery unit and a Tail Gas Treatment unit.

The following examples provide another illustration of the invention without providing any limitation. They have been carried out with DMDS which is one of the components of DSO. It is expected that the same results for $H_2S$ production would be obtained with DSO.

EXAMPLES: CATALYTIC CONVERSION TESTS IN VAPOR PHASE OF DIMETHYLDISULFIDE (DMDS)

Material and Method

The catalytic conversion in vapor phase of a gaseous mixture of $DMDS/N_2$ (contact time, $\tau=0.24$ g·s·cm$^{-3}$; DMDS concentration $C_{DMDS}$=3400 ppmv) was performed in a fixed bed microreactor wherein 100 mg of catalyst (particles size=150-250 µm) is placed. The catalyst was activated "in-situ" under air, at 550° C., during 6 h, just before the test.

The microreactor is placed in a vertical oven equipped with an electronic controller-regulator and a thermocouple inserted in the catalytic bed to measure and control the temperature. The tests were performed at 550° C. The reaction time is 18 h or 42 h.

The product obtained are analyzed by a gas chromatograph (Shimadzu GC 2014) connected to the reactor by an exit line heated at 100° C. The concentrations of DMDS and methanethiol ($CH_3SH$) are determined using calibration curves. The concentrations of the other products containing sulfur such as $CS_2$ and dimethylsulfide (DMS) have been calculated on the basis of the response factor of $CH_3SH$.

Catalysts

The activity of Co-gamma-$Al_2O_3$ according to the invention was tested and compared to commercial gamma-$Al_2O_3$, zeolite HZSM5-15 and synthesized Co-HZSM5-15 catalysts.

Commercial Catalysts Zeolite HZSM5-15 (CBV 3024E, Si/Al=15) was purchased from Zeolyst International.

Gamma-$Al_2O_3$(No UE=215-691-6) was purchased from Alfa Aesar.

Synthesis of Co-Gamma-$Al_2O_3$

Co-gamma-$Al_2O_3$, having 2.5 wt % of cobalt, was synthesized by impregnating the purchased gamma-$Al_2O_3$ with a volume of an aqueous solution of $Co(NO_3)_2$*$6H_2O$ equal to the pores volume of the catalyst and having a cobalt amount corresponding to the desired final weight percentage of cobalt on the gamma-$Al_2O_3$. After the impregnation, the resulting material was recovered to be dried in an oven overnight before to be calcinated at 550° C. during 8 h.

Synthesis of Co-HZSM5-15

Co-HZSM5-15 was synthesized following the same protocol as Co-gamma-$Al_2O_3$ applied to the purchased zeolite HZSM5-15.

Catalyst Characterization

The particles size is determined by mechanical screening. Only the catalysts having a particle size from 150 µm to 250 µm are studied.

The content of cobalt relative to gamma-$Al_2O_3$ and HZSM5-15 is determined by EDX using a Fei Quanta 200F Scanning Electron Microscope.

Specific surface and pores volume were determined by BET measurements using the ASAP 2020 Micromeritics.

To evaluate the amount of coke deposited on the surface of the spent catalysts, said spent catalysts were analyzed by thermogravimetric analysis (TGA) using a TG-DSC 111 (SETARAM). The chemical species adsorbed on the surface of the spent catalyst after the catalytic conversion test were first eliminated by sweeping the microreacteur with a gaseous stream of nitrogen at 550° C. 20 mg of the spent catalyst were then recovered from the microreactor to be heated, in the TG-DSC 111, under air from room temperature to 800° C. at 10° C.*min$^{-1}$. The loss weight between 400° C. and 800° C. was assigned to the combustion of coke.

The properties of the catalysts are summarized in the following Table 1.

TABLE 1

Catalysts properties

| Catalyst | Specific surface (m$^{2}$*g$^{-1}$) | Pores volume (cm$^{3}$*g$^{-1}$) |
|---|---|---|
| Co-gamma-Al$_2$O$_3$ | 226 | 0.71 |
| gamma-Al$_2$O$_3$ | 249 | 0.78 |
| HZSM5-15 | 378 | 0.26 |
| Co-HZSM5-15 | 343 | 0.24 |

Example 1: Catalytic Conversion Tests of Co-Gamma-Al$_2$O$_3$ and Gamma-Al$_2$O$_3$ The tests were performed at 550° C., during 18 h, with the above described gaseous mixture of DMDS/N$_2$.

a) In the Absence of Water.

Since no DMDS is measured at the exit of the microreactor, the conversion of DMDS by Co-gamma-Al$_2$O$_3$ and gamma-Al$_2$O$_3$, in the absence of water, is complete and leads to the formation of CH$_4$ and CS$_2$ and not to DMS and CH$_3$SH.

Figure 4:
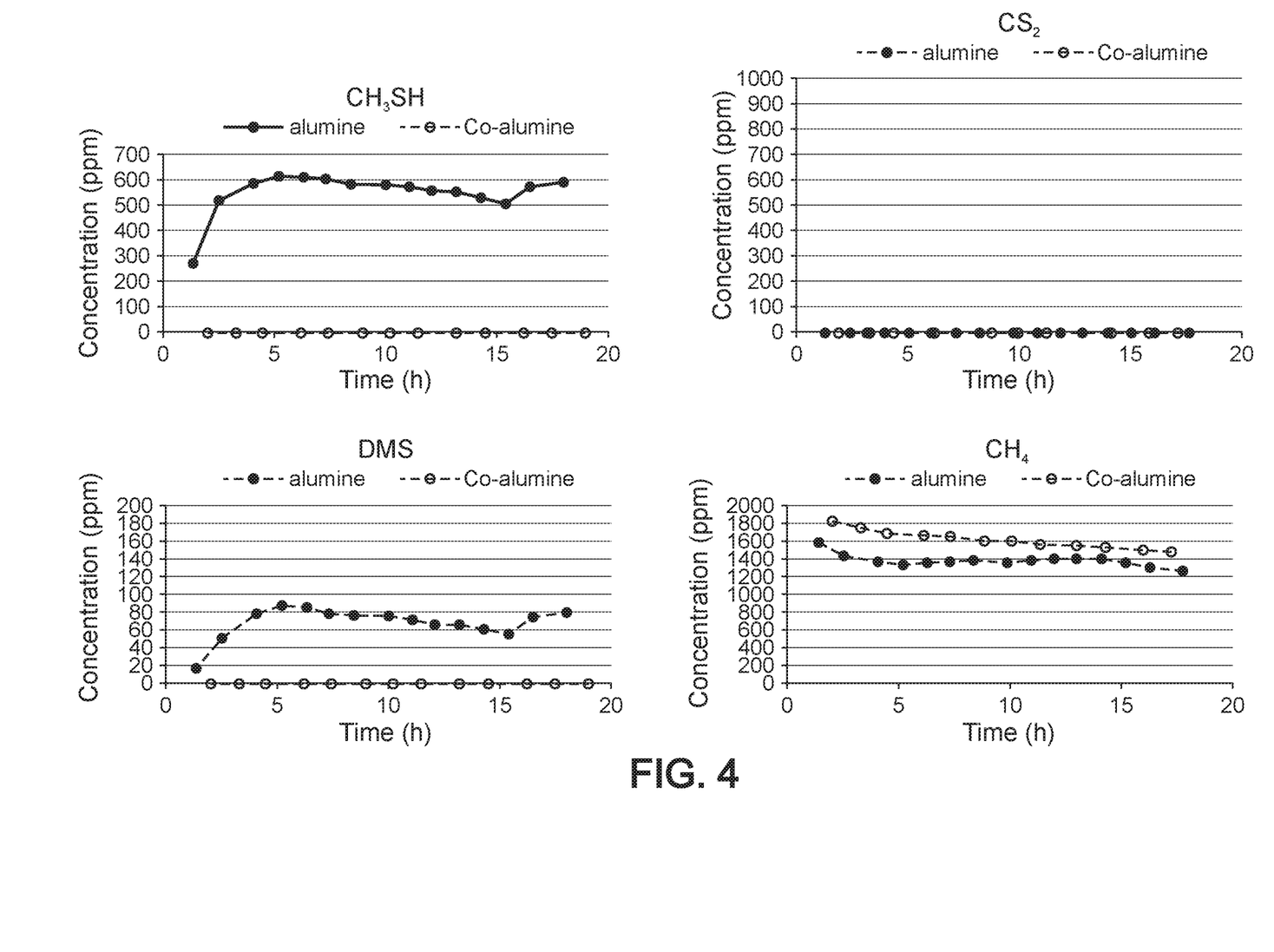
FIG. 4 represents the concentration of methanethiol ($CH_3SH$), $CS_2$, dimethylsulfide (DMS) and methane ($CH_4$) obtained during the catalytic conversion of DMDS with Co-gamma-$Al_2O_3$ or gamma-$Al_2O_3$ in the absence of water as a function of time over 18 hours (h).

As illustrated on the FIG. 4, the addition of cobalt to gamma-Al$_2$O$_3$ leads to a slight increase in the concentration of CS$_2$ obtained by the catalytic conversion of DMDS. The concentrations of CH$_3$SH, DMS and CH$_4$ obtained are similar for Co-gamma-Al$_2$O$_3$ and gamma-Al$_2$O$_3$.

Moreover, during the 18 h of the test, Co-gamma-Al$_2$O$_3$ and gamma-Al$_2$O$_3$ are not deactivated.

At the end of the test, the amount of coke deposited on the surface of gamma-Al$_2$O$_3$ is 27 mg, and the amount on the surface of Co-gamma-Al$_2$O$_3$ is 27.7 mg.

b) In the Presence of Water (Ratio H$_2$O/DMDS=1.4)

Since no DMDS is measured at the exit of the microreactor, the conversion of DMDS by Co-gamma-Al$_2$O$_3$ and gamma-Al$_2$O$_3$, in the presence of water, is complete.

Figure 5:
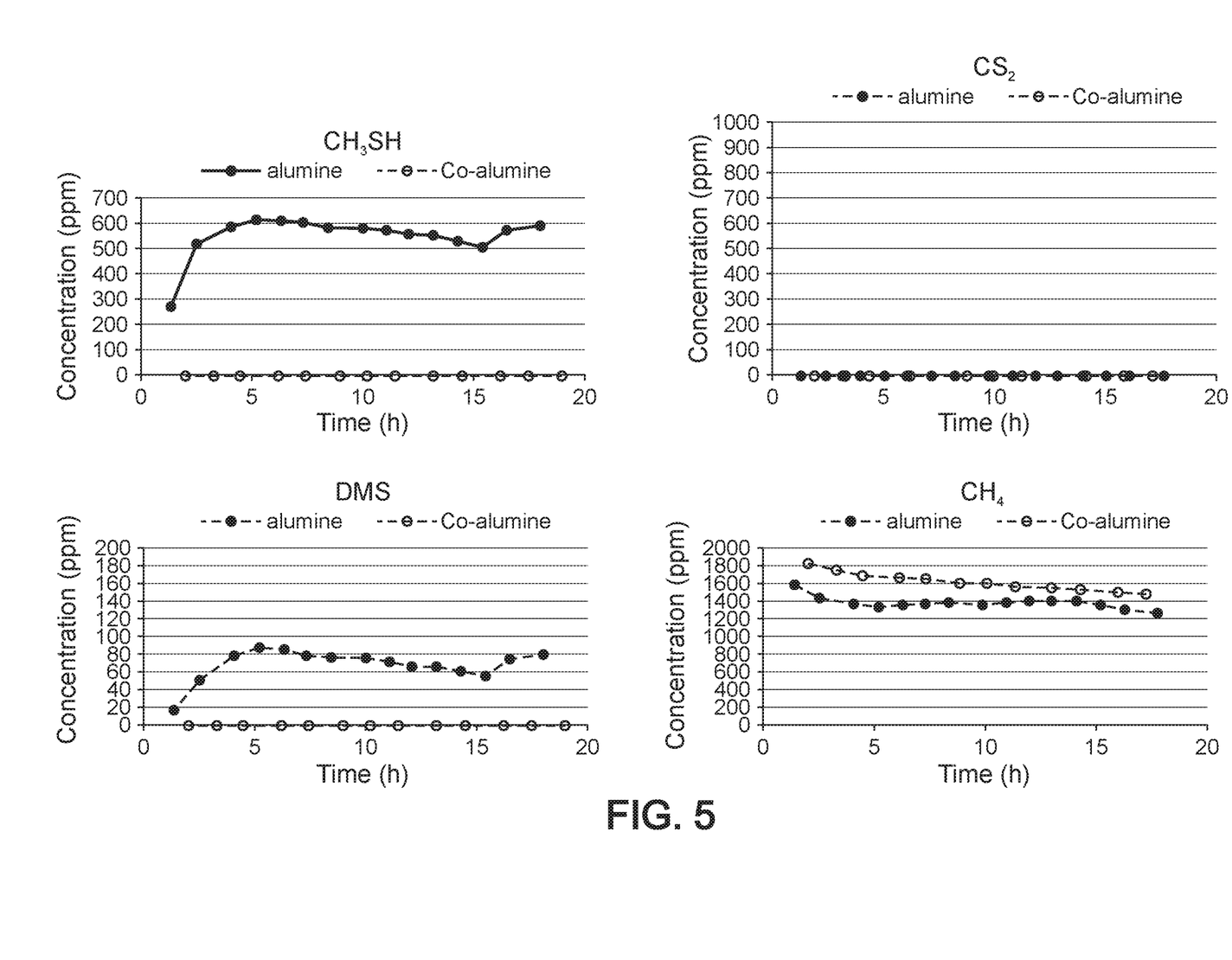
FIG. 5 represents the concentration of methanethiol ($CH_3SH$), $CS_2$, dimethylsulfide (DMS) and methane ($CH_4$) obtained during the catalytic conversion of DMDS with Co-gamma-$Al_2O_3$ or gamma-$Al_2O_3$ in the presence of water as a function of time over 18 h.

As illustrated on the FIG. 5, the addition of cobalt to gamma-Al$_2$O$_3$ leads to the complete conversion of DMDS into CH$_4$ only and the concentration of CH$_4$ obtained is higher than the one obtained with gamma-Al$_2$O$_3$. Moreover, the presence of water leads to the complete hydrolysis of CS$_2$ into CO$_2$ and H$_2$S (the concentration of CO$_2$ and H$_2$S are not presented in the FIG. 5).

During the 18 h of the test, Co-gamma-Al$_2$O$_3$ and gamma-Al$_2$O$_3$ are not deactivated during the test.

Finally, the presence of water leads to an important decrease of the amount of coke deposited on the surface of the catalysts at the end of the test. Indeed, only 3.8 mg coke is deposited on the surface of gamma-Al$_2$O$_3$, and only 9.7 mg is deposited on the surface of Co-gamma-Al$_2$O$_3$.

c) Conclusion.

Co-gamma-Al$_2$O$_3$ and gamma-Al$_2$O$_3$ are not deactivated during these two tests.

Moreover, the presence of water greatly reduces the amount of coke deposited on the surface of the catalysts.

In the absence or in the presence of water, the catalytic conversion of DMDS by gamma-Al$_2$O$_3$ leads to the formation of non-recoverable products (CS$_2$ in the absence of water, CH$_3$SH and DMS in the presence of water).

The combination of the addition of cobalt to gamma-Al$_2$O$_3$ and the presence of water leads to the complete conversion of DMDS into CH$_4$ and the complete hydrolysis of CS$_2$ into CO$_2$ and H$_2$S.

Based on the results of Example 1, it is expected that Co-gamma-Al$_2$O$_3$ would catalytically convert DSO in vapor phase into CH$_4$, CS$_2$ and +H$_2$S in absence of water, and catalytically convert DSO in vapor phase into CH$_4$ and H$_2$S in presence of water.

Example 2: Comparative Tests with HZSM5-15 and Co-HZSM5-15

The tests were performed at 550° C., during 18 h, with the above described gaseous mixture of DMDS/N$_2$.

a) In the Absence of Water.

Since no DMDS is measured at the exit of the microreactor, the conversion of DMDS by HZSM5-15 and Co-HZSM5-15, in the absence of water, is complete.

Figure 6:
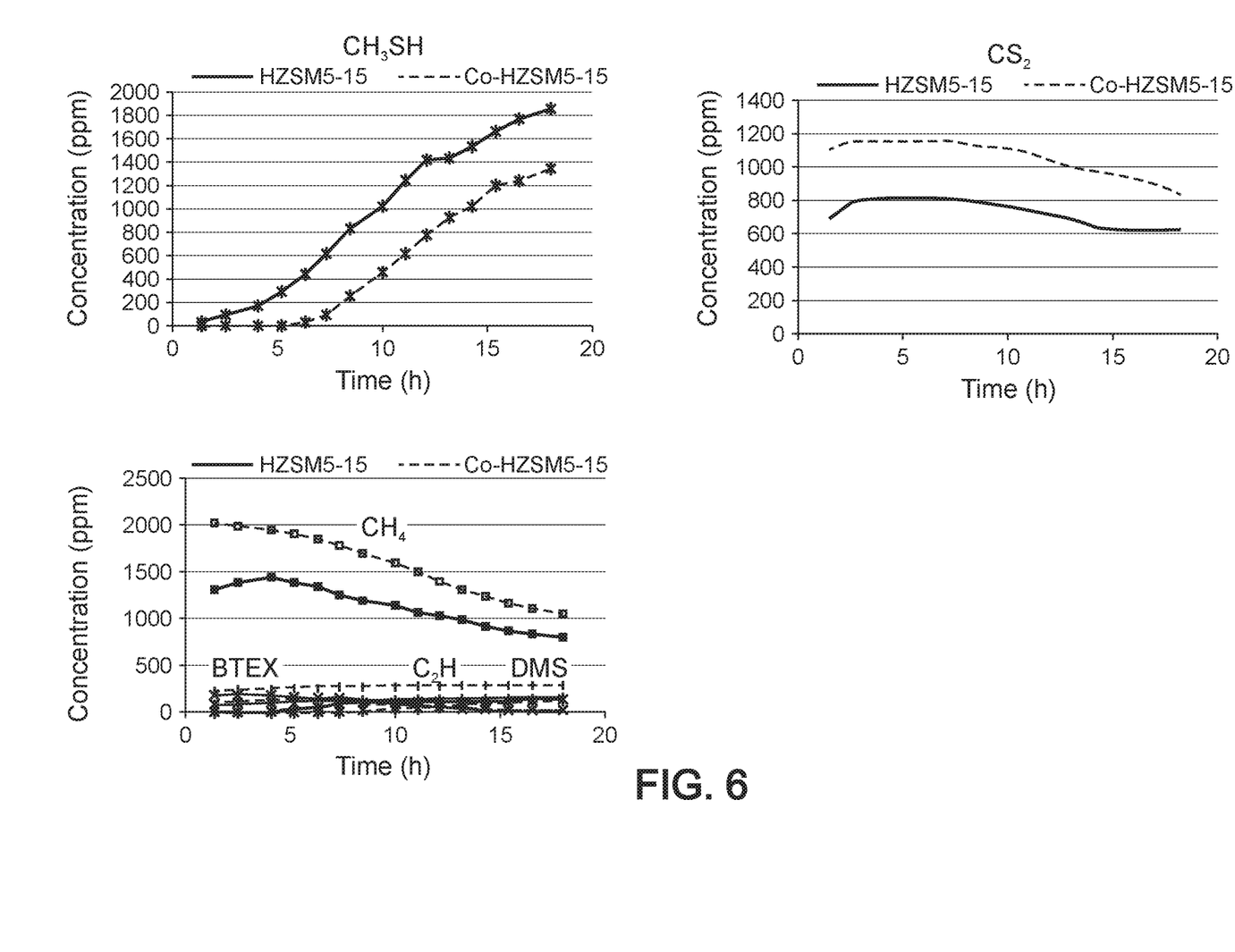
FIG. 6 represents the concentration of methanethiol ($CH_3SH$), $CS_2$, dimethylsulfide (DMS), methane ($CH_4$) and impurities (ethylene, $C_2H_4$ and BTEX, referring to benzene, toluene, ethylbenzene, and xylenes) obtained during the catalytic conversion of DMDS with Co-HZSM5-15 or HZSM5-15 in the absence of water as a function of time over 18 h.

However, as illustrated on the FIG. 6, the conversion of DMDS by HZSM5-15 leads to the important formation of CH$_3$SH and CS$_2$ all along the test. The addition of cobalt to HZSM5-15 simply delays the formation of CH$_3$SH and increases the amount of CS$_2$ formed. At the end of the tests, the amount of coke deposited on the surface of the HZSM5-15 is 26 mg, and the amount on the surface of Co-HZSM5-15 is 17 mg.

b) In the Presence of Water (Ratio H$_2$O/DMDS=1.4)

Since no DMDS is measured at the exit of the microreactor, the conversion of DMDS by HZSM5-15 and Co-HZSM5-15, in the presence of water, is complete.

Figure 7:
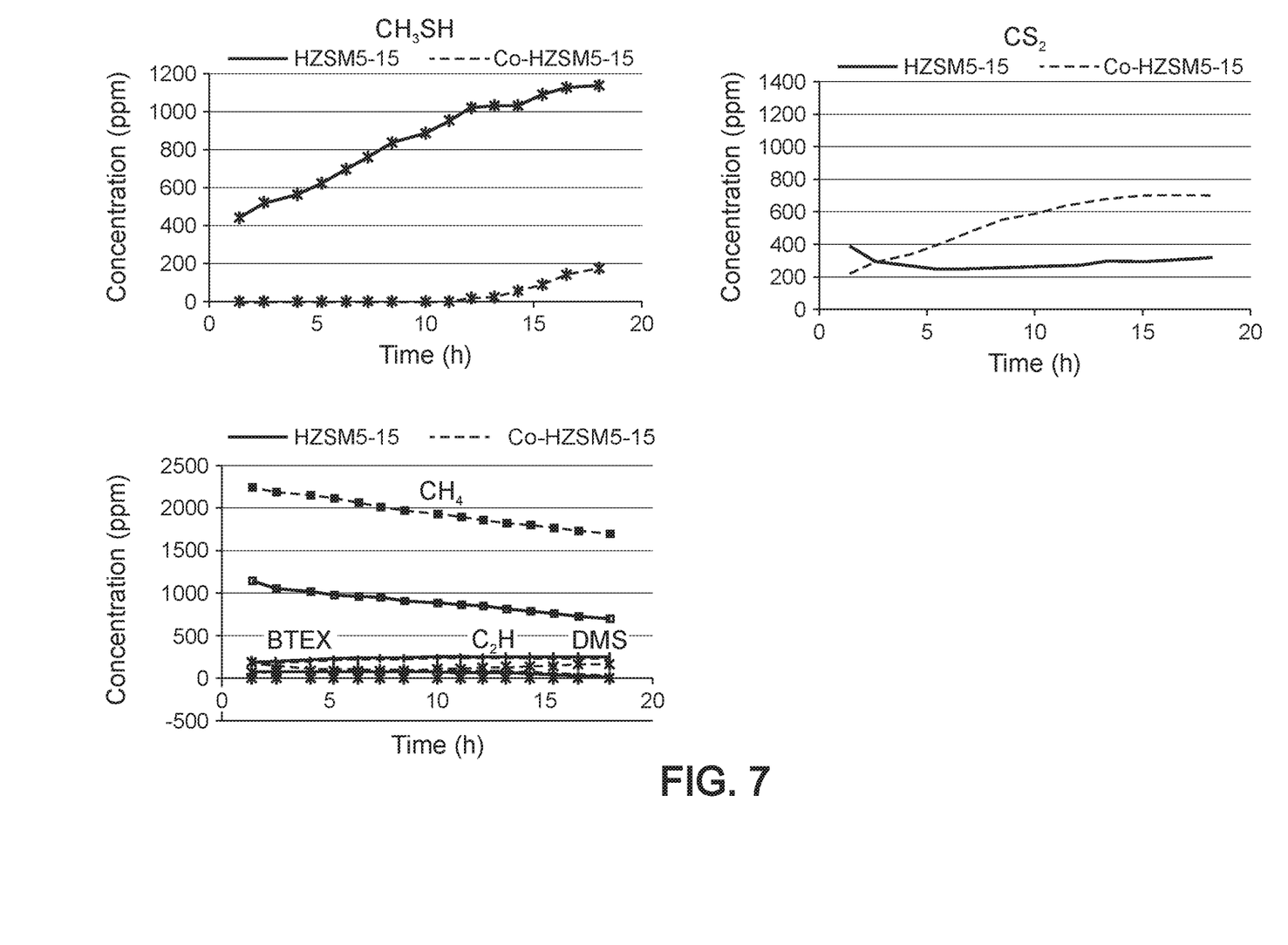
FIG. 7 represents the concentration of methanethiol ($CH_3SH$), $CS_2$, dimethylsulfide (DMS), methane ($CH_4$) and impurities (ethylene, $C_2H_4$ and BTEX, referring to benzene, toluene, ethylbenzene, and xylenes) obtained during the catalytic conversion of DMDS with Co-HZSM5-15 or HZSM5-15 in the presence of water as a function of time over 18 h.

As illustrated by the FIG. 7, HZSM5-15 still converts DMSD into CH$_3$SH and CS$_2$ is not completely hydrolyzed into CO$_2$ and H$_2$S.

As illustrated by the FIGS. 6 and 7, Co-HZSM5-15 still converts DMDS into CH$_3$SH, even if the presence of water further delays said conversion. CS$_2$ is also not completely hydrolyzed into CO$_2$ and H$_2$S.

At the end of the tests, the amount of coke deposited on the surface of the HZSM5-15 is 18 mg, and the amount on the surface of Co-HZSM5-15 is 8.4 mg.

c) Conclusion.

In the absence or in the presence of water, the catalytic conversion of DMDS by HZSM5-15 and Co-HZSM5-15 leads to the formation of non-recoverable products such as CH$_3$SH. Moreover, in the presence of water, the hydrolysis of CS$_2$ is not complete.

Therefore, it is expected that the catalytic conversion of DSO in the operating conditions of Example 2 would not be satisfactory.

Example 3: Long Term Test of Co-Gamma-Al$_2$O$_3$ in the Presence of Water (Ratio H$_2$O/DMDS=1.4)

The test was performed at 550° C., during 42 h with the above described gaseous mixture of DMDS/N$_2$.

Figure 8:
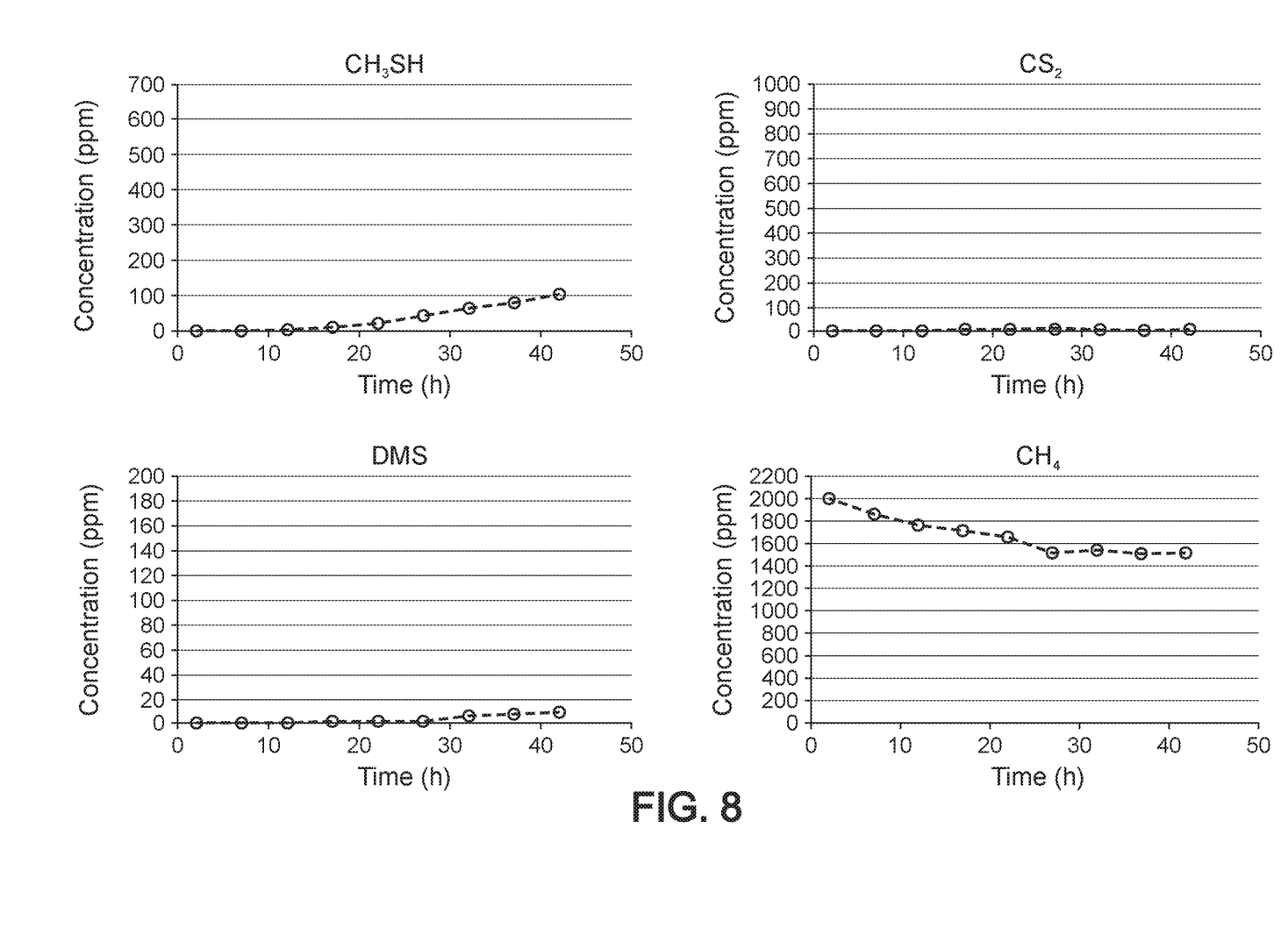
FIG. 8 represents the concentration of methanethiol ($CH_3SH$), $CS_2$, dimethylsulfide (DMS) and methane ($CH_4$) obtained during the catalytic conversion of DMDS with Co-gamma-$Al_2O_3$ in the presence of water as a function of time over 42 h.

As illustrated on the FIG. 8, the conversion of DMDS into CH$_4$ and the hydrolysis of CS$_2$ are complete during the 42 h of the test. Nevertheless, marginal amounts of DMS and CH$_3$SH are obtained after 22 h.

Based on the results of Example 3, it is expected that Co-gamma-Al$_2$O$_3$ would efficiently catalytically convert DSO in vapor phase into CH$_4$ and H$_2$S in presence of water during more than 40 h.

Example 4: Regenerability of Spent Co-Gamma-Al$_2$O$_3$ Catalyst

Figure 9:
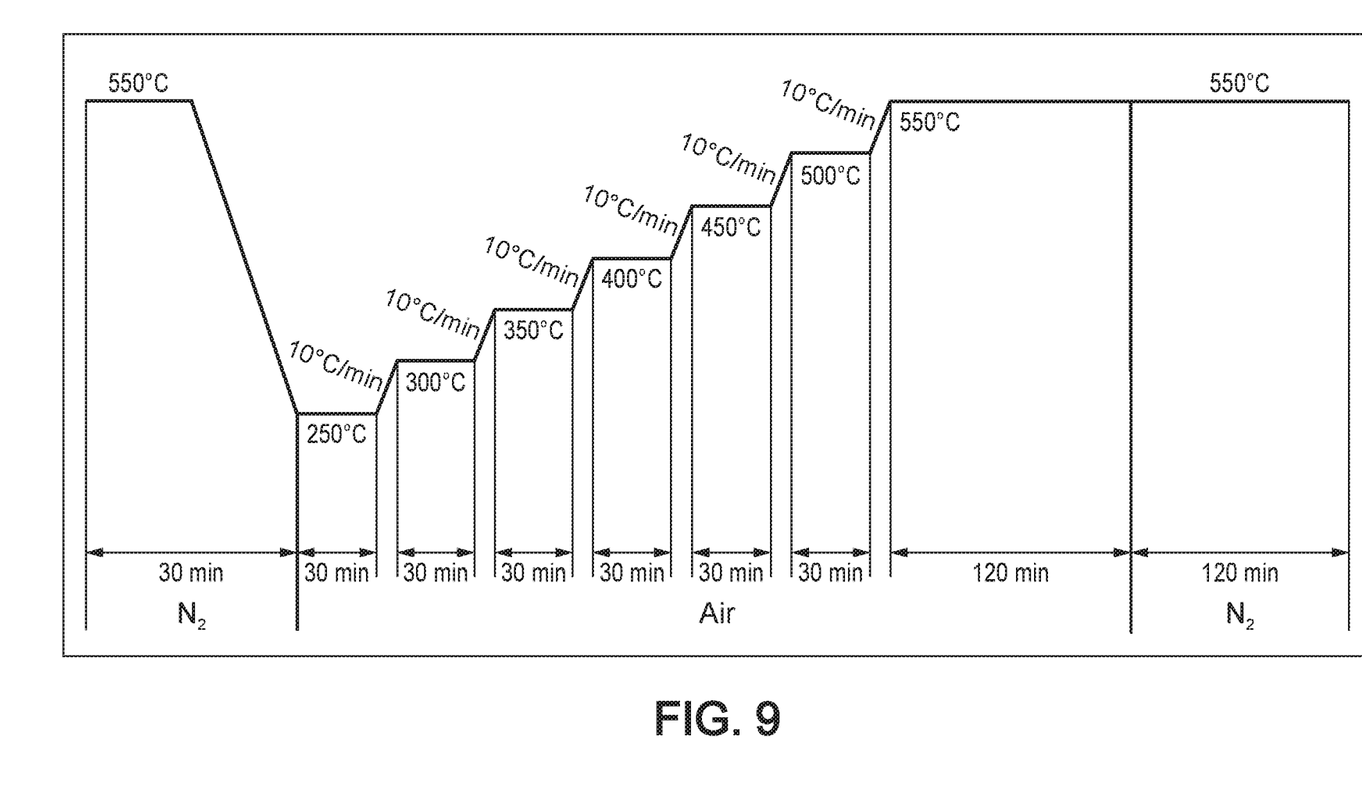
FIG. 9 represents the regeneration protocol of the spent Co-gamma-$Al_2O_3$ after the 42 h test.

After the long term test of the Example 3, the spent Co-gamma-Al$_2$O$_3$ catalyst is regenerated under air according to the protocol depicted on the FIG. 9.

Figure 10:
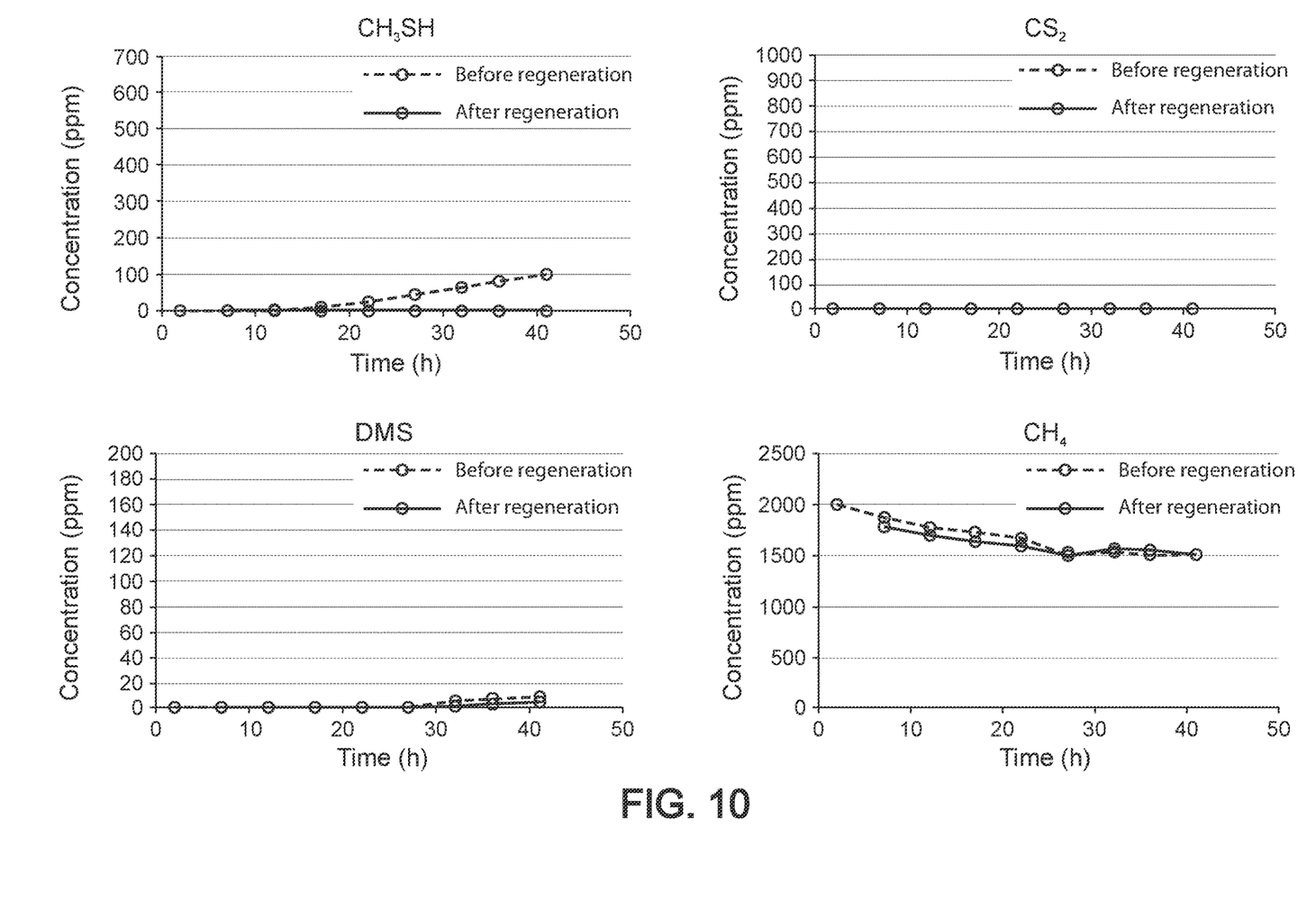
FIG. 10 represents the concentration of methanethiol ($CH_3SH$), $CS_2$, dimethylsulfide (DMS) and methane ($CH_4$) obtained during the catalytic conversion of DMDS with the regenerated Co-gamma-$Al_2O_3$ in the presence of water as a function of time over 42 h.

The long term test of the Example 3 is then performed on the regenerated Co-gamma-Al$_2$O$_3$ catalyst. As illustrated on the FIG. 10, the catalytic properties of the Co-gamma-Al$_2$O$_3$ are restored (complete conversion of DMDS into a CH$_4$ and complete hydrolysis of CS$_2$) and even improved (no CH$_3$SH is obtained after 22 h, while the amount of DMS obtained after 22 h is reduced). These results underline the regenerability of the Co-gamma-Al$_2$O$_3$ catalyst.

Based on the results of Example 4, it is expected that Co-gamma-Al$_2$O$_3$ would efficiently catalytically convert DSO in vapor phase into CH$_4$ and H$_2$S in presence of water after being regenerated. Co-gamma-Al$_2$O$_3$ would thus be used several times.

The invention claimed is:

1. A method for the catalytic conversion in vapor phase of disulfide oil into methane and hydrogen sulfide, the method comprising contacting disulfide oil with a supported transition metal catalyst,
   wherein contacting disulfide oil with the supported transition metal catalyst is performed in the presence of water.

2. The method according to claim 1, wherein the supported transition metal catalyst comprises a support chosen from alumina (Al$_2$O$_3$), silica, titania (TiO$_2$) or a mixture thereof.

3. The method according to claim 2, wherein the alumina is alpha-alumina, gamma-alumina, delta-alumina, or theta-alumina.

4. The method according to claim 1, wherein the supported transition metal catalyst comprises a transition metal, wherein the transition metal is manganese, iron, cobalt, nickel, copper, zinc, molybdenum, ruthenium, rhodium or a mixture thereof.

5. The method according to claim 1, wherein the content of a transition metal in the supported transition metal catalyst relative to a support is 0.1 wt % to 10 wt %.

6. The method according to claim 5, wherein the content of a transition metal in the supported transition metal catalyst relative to a support is 2.2 wt % to 2.7 wt %.

7. The method according to claim 1, wherein the molar ratio of water in the vapor phase comprising disulfide oil to disulfide oil is 0.1 to 10.

8. The method according to claim 1, wherein contacting disulfide oil with the transition metal catalyst is performed at a temperature from 350° C. to 700° C.

9. The method according to claim 1, further comprising a step of oxidative regeneration of a spent supported transition metal catalyst.

10. The method according to claim 9, wherein the oxidative regeneration is performed in the presence of air.

11. The method according to claim 1, wherein the molar ratio of water in the vapor phase comprising disulfide oil to disulfide oil is 1.4 to 4.

12. The method according to claim 1, wherein contacting disulfide oil with the transition metal catalyst is performed at a temperature from 540° C. to 560° C.

13. A catalytic conversion unit for the catalytic conversion in vapor phase of disulfide oil into methane and hydrogen sulfide, the catalytic conversion unit comprising a catalytic reactor comprising:
   a vapor feed line to feed the catalytic reactor with a vapor phase of disulfide oil,
   a gas recover line to recover a gaseous stream comprising methane and H$_2$S, and
   at least one catalytic bed wherein a supported transition metal catalyst is placed,
wherein the catalytic conversion unit further comprises:
   a vapor generator unit for generating the vapor phase of disulfide oil and fluidly connected to the vapor feed line of the catalytic reactor,
   a liquid feed line to feed the vapor generator unit with liquid disulfide oil, and a water reactor for providing liquid water or water steam to the catalytic conversion unit through a water line.

14. The catalytic conversion unit according to claim 13, wherein the water line is fluidly connected to one or more of the liquid feed line, the vapor generator unit, the vapor feed line and the catalytic reactor.

15. The catalytic conversion unit according to claim 13, wherein the water reactor is fed with the vapor phase of disulfide oil by the vapor feed line and is fluidly connected to the catalytic reactor through a water enriched DSO line.

16. The catalytic conversion unit according to claim 13, further comprising:
   a separation unit fed by the gas recover line of the catalytic reactor for separating methane from hydrogen sulfide of the gaseous stream,
   a methane line to recover methane, and
   an hydrogen sulfide line to recover hydrogen sulfide.

17. The catalytic conversion unit according to claim 16, further comprising a sulfur recovery unit fed by the hydrogen sulfide line and having a sulfur exit line for recovering elemental sulfur and a gas exit line for recovering a tail gas stream.

* * * * *